United States Patent [19]

Fauner

[11] 4,248,097

[45] Feb. 3, 1981

[54] TORSION SHEAR APPARATUS

[76] Inventor: Gerhard Fauner, Röntgenstrasse 10, D-8032 Lochham, Fed. Rep. of Germany

[21] Appl. No.: 26,564

[22] Filed: Apr. 3, 1979

[30] Foreign Application Priority Data

Apr. 5, 1978 [DE] Fed. Rep. of Germany ....... 2814786

[51] Int. Cl.³ .......................... G01N 3/22; G01N 3/24
[52] U.S. Cl. .......................................... 73/842; 73/848
[58] Field of Search ................ 73/847, 842, 848, 850, 73/856, 860, 150 A, 843

[56] References Cited

U.S. PATENT DOCUMENTS

| | | | |
|---|---|---|---|
| 233,712 | 10/1880 | Thurston | 73/847 |
| 926,513 | 6/1909 | Souther | 73/848 |

*Primary Examiner*—Anthony V. Ciarlante
*Attorney, Agent, or Firm*—Finnegan, Henderson, Farabow, Garrett & Dunner

[57] ABSTRACT

A torsion shear apparatus, especially for testing adhesives, in which two members of a test specimen bonded one into the other are subjected to a torsional load, comprising a rigid retainer for non-rotatable and form-locked retention of the first member of the test specimen, an operating member rotatably mounted in a radial bearing system in horizontal alignment with the retainer and adapted for form-locked and non-rotatable engagement with the second member of the test specimen, and a torsion-applying device for rotating the operating member relative to the retainer, characterized in that the operating member comprises a web connecting two radial bearings, each supported in a bearing support, the web being engaged by a horizontal load lever forming the torsion-applying device, and in that the retainer comprises a sliding guide portion having guide surfaces extending transversely of the radial bearings and permitting radial displacement of the first test specimen member.

8 Claims, 5 Drawing Figures

TORSION SHEAR APPARATUS

This invention relates to a torsion shear apparatus, especially for testing adhesives.

For testing the bonding strength of adhesives, it is known to bond two flat metal strips to one another in overlapping relationship and to subject the bonded strips to a load in a pull-test machine. It is further known to bond two test specimens to one another in abutting relationship and to subject the bonded test specimens to a torsional load. In a further testing method, a conical first portion of a test specimen is bonded to an inner surface of a correspondingly shaped second socket portion, whereupon the two members are subjected to a torsional load. In the above-named adhesive testing methods, care must be taken in designing the test specimens so as to enable the two portions to be bonded to one another to be compressed to achieve setting of the adhesive. New testing standards are being established with the arrival of anaerobic adhesives which do not require the application of pressure for setting. Of particular importance in this context is the testing of torsional shear resistance, due to its practical applicability, since the most interesting cases of employ are in the field of connections between rotation-symmetric members fitting into one another, such as bonding of hubs on shafts, bolts or pins in bores and tubes etc. A testing apparatus for testing torsional shear resistance should meet the following requirements:
 simple construction and ease of operation,
 testing ability for simple test specimens,
 adaptability to standard testing machines, and
 the load is to be applied such that a pure torsional shear load occurs in the bonding layer, or between the bonding layer and the bond surfaces, respectively.

West German Patent No. 1,141,807 discloses a prior art torsion shear apparatus of the type set forth above. For testing the bonding strength of an adhesive in this prior art apparatus, two conically shaped members of a test specimen are bonded to one another and subjected to a torsional load. To this end, the first member of the specimen is non-rotatably inserted into a rigid retainer having a splined interior surface for form-locked engagement with a splined outer surface of the first specimen member. The operating member of the apparatus is rotatably supported in a radial bearing in horizontal alignment with the retainer member. The operating member is likewise provided with interior splines for form-locked engagement with complementary outer splines formed on the second specimen member, so that the latter is non-rotatably retained in the operating member. A torsional force applying means comprising a sheave is fixedly attached to the operating member. A pull-rope is guided around the sheave, with one of its ends affixed to the sheave and its other end connected to the pulling head of a pull-test machine. The retainer is fixedly supported on the base of the testing machine.

For testing an adhesive, the test specimen, consisting of the two conical members bonded to one another, is inserted into the retainer and the operating member so that the splines provided on the two test specimen members are engaged with the complementary splines of the retainer and the operating member, respectively. The rope carried by the sheave is then subjected to tensional load, whereby a torsional load is applied to the test specimen. This prior art apparatus is of relatively sophisticated design. In order to ensure that a pure torsional load is achieved, the retainer and the operating member have to be precisely centered, since the test specimen might otherwise be subjected to bending loads falsifying the testing result. In addition, insertion of the test specimen into the apparatus is relatively complicated, since care has to be taken that the rotatable operating member is positioned with respect to the retainer such that the splines of both specimen members may become engaged with the respective interior splines.

It is an object of the invention to provide a torsion shear apparatus of the type set forth above which, while being of simple design, ensures that a pure torsional load in occurs the bonding layer.

Proceeding from a prior art torsion shear apparatus of the type set forth above, this object is attained in accordance with the invention by providing a torsion shear apparatus, especially for testing adhesives, in which two members of a test specimen bonded one into the other are subjected to a torsional load, comprising rigid retainer means for non-rotatable and form-locked retention of the first member of the test specimen, an operating member rotatably mounted in a radial bearing system in horizontal alignment with the retainer means and adapted for form-locked and non-rotatable engagement with the second member of the test specimen, and torsion applying means for rotating the operating member relative to the retainer means, characterized in that the operating member comprises a web connecting two radial bearings each supported in a bearing support, the web being engaged by a horizontal load lever forming the torsion applying means, and in that the retainer means comprises a sliding guide portion having guide surfaces extending transversely of the radial bearings and permitting radial displacement of the first test specimen member.

The torsion shear apparatus according to the invention is of simple design and adapted for employ as an accessory in conventional standard testing machines. The end of the load lever may, for instance, be loaded by the plunger of a pressure testing machine. The sliding guide member, with its guide surfaces, permits the portion of the test specimen received therein to be of rectangular configuration, for instance, or round with flattened side surfaces. Since the sliding guide permits radial movements of the test specimen, the occurrence of undesirable bending loads is prevented. A retainer device of this configuration further permits rapid and uncomplicated insertion of the test specimen.

A particularly advantageous embodiment of the invention is due to the fact that a further operating member of similar configuration is located symmetrically to the aforesaid operating member on the opposite side of the retainer means, the further operating member having a second horizontal lever, the ends of the two levers being interconnected to form a twin load lever. A torsion shear apparatus of this design permits the load lever to be engaged simultaneously with both projecting ends of a bolt bonded to a surrounding sleeve, while the sleeve is non-rotatably retained in the retainer device. This arrangement is particularly suited for the above-discussed testing of anaerobic adhesives.

The embodiment of the invention wherein the web has two parallel flattened surfaces for engagement by a fork-shaped configuration of the load lever is characterized by a very simple design and particularly simple operation.

An embodiment of the invention shall now be explained in detail with reference to the accompanying drawings, wherein:

DESCRIPTION OF THE PREFERRED EMBODIMENT

Figure 1:
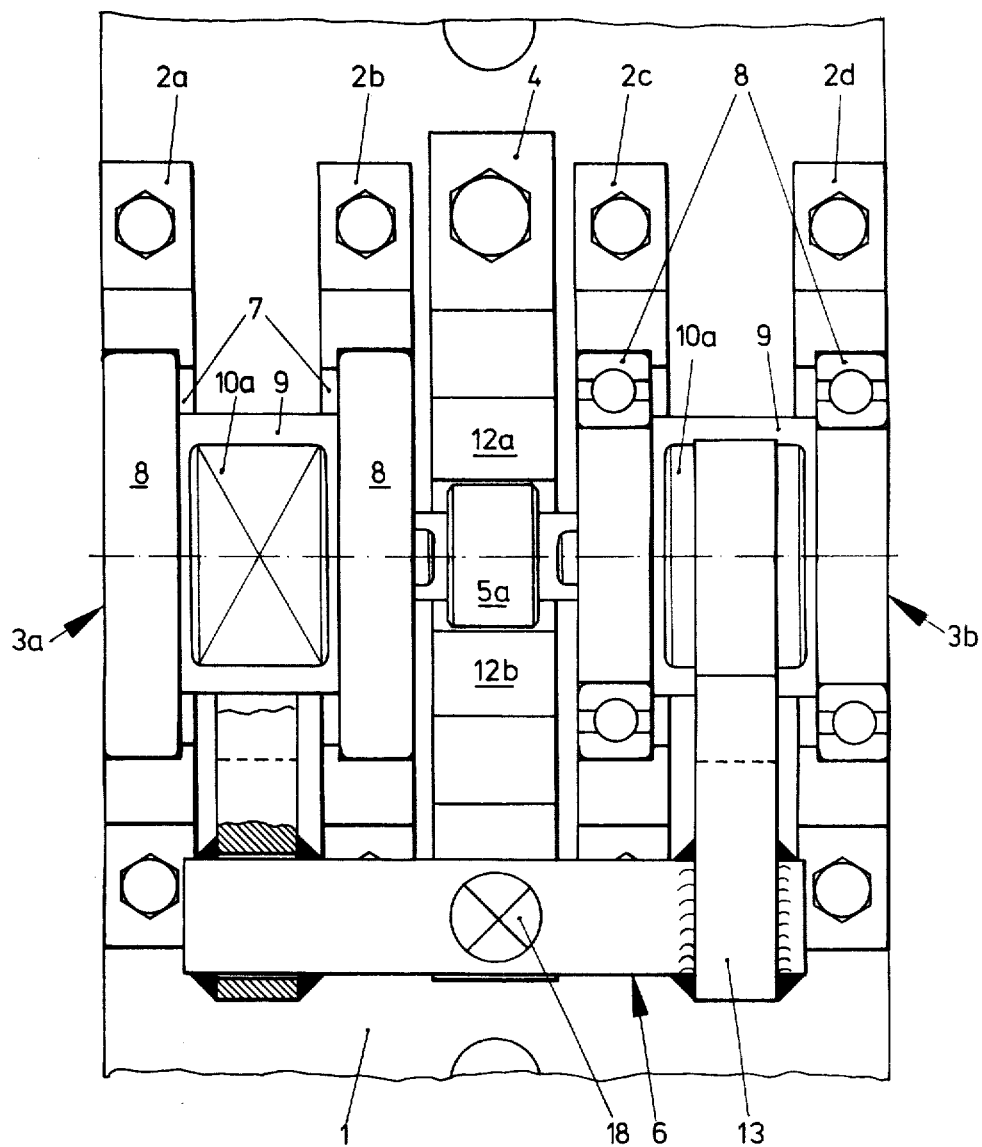
FIG. 1 shows a top plan view of a torsion shear apparatus for two-ended torsional loading in accordance with the present invention.
Figure 2:
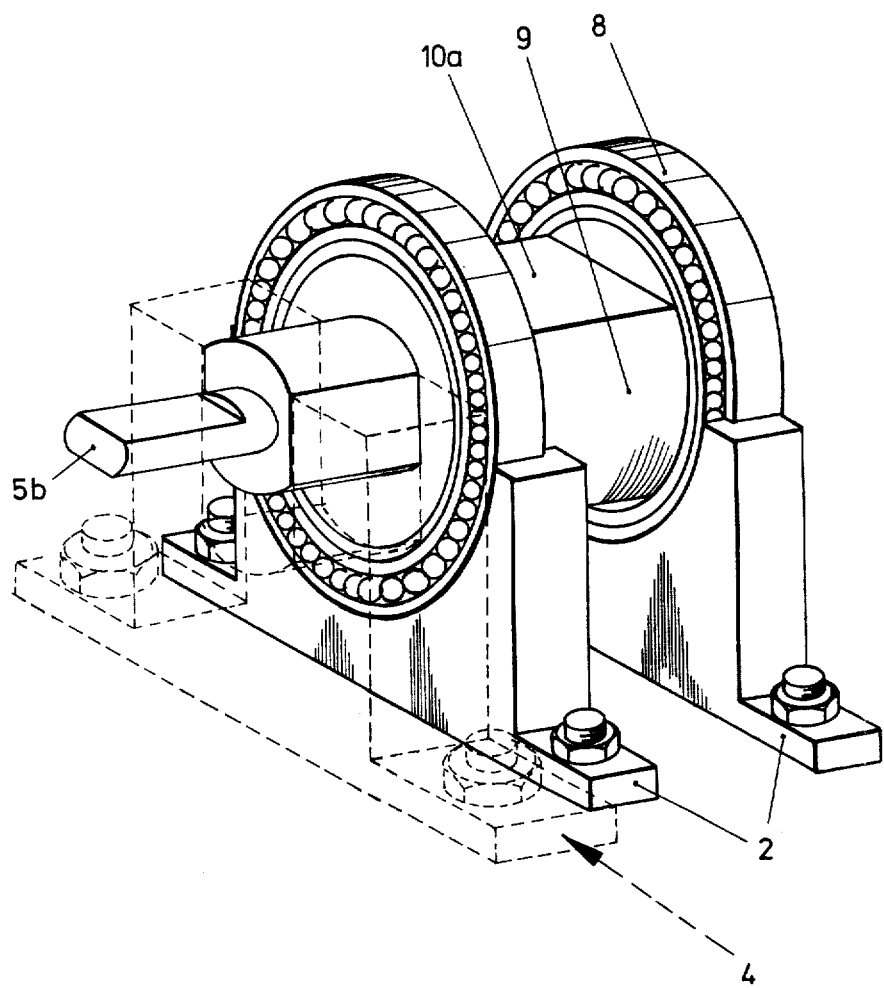
FIG. 2 shows a perspective view of a portion of the apparatus shown in FIG. 1.
Figure 3:
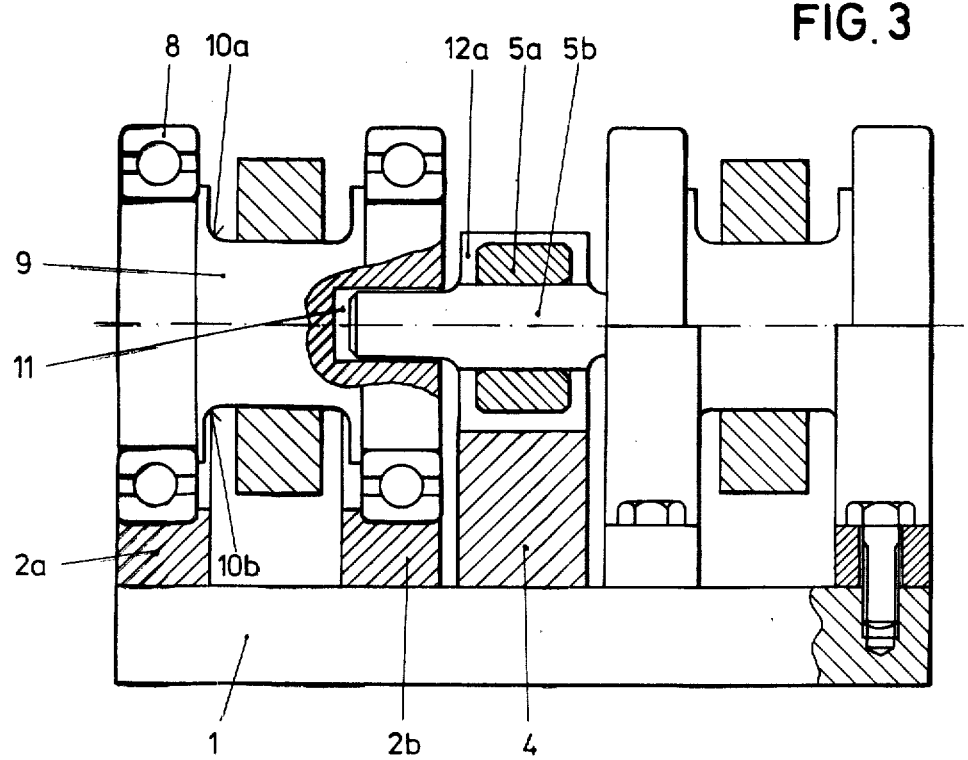
FIG. 3 shows a partially sectioned elevational view of the apparatus shown in FIG. 1.

FIG. 1 shows a base plate 1 carrying four bearing cradles 2a-2d bolted thereon. Base plate 1 may be mounted on any universal testing machine. Mounted in bearing cradles 2a, 2b and 2c, 2d are torsion means 3a and 3b, respectively. Between bearing cradles 2b and 2c a retainer means 4 is mounted by means of bolts. A U-shaped guiding recess is provided in retainer means 4 for non-rotatable retention of a sleeve member 5a of a test specimen 5. The two projecting ends of a bolt 5b bonded to the interior of sleeve 5a of test specimen 5 are in form-locked engagement with the two torsion means 3a, 3b, the torsion means being engaged by a twin load lever 6.

Bearing cradles 2a to 2d are each of semicircular configuration and have oppositely disposed pairs of ridges 7 for locating the torsion means in the axial direction. The bearing cradles are open at the top.

Each torsion means 3a, 3b consists of two radial bearings 8 connected to one another by a web 9. Web 9 is formed as a shaft having two oppositely disposed, parallel flattened surfaces 10a, 10b. Each web 9 is formed with a rectangular recess 11 located in symmetric relationship to the axis of rotation for form-locked engagement with a portion of the test specimen.

Retainer means 4 is of substantially U-shaped cross-sectional configuration, having two parallel, vertically extending guide elements 12a, 12b. Guide elements 12a, 12b define a sliding guide which is open at the top and extends downward in the direction of base plate 1, so that any applicable test specimen has sufficient vertical play without being operatively supported by the bottom of the sliding guide.

Figure 5:
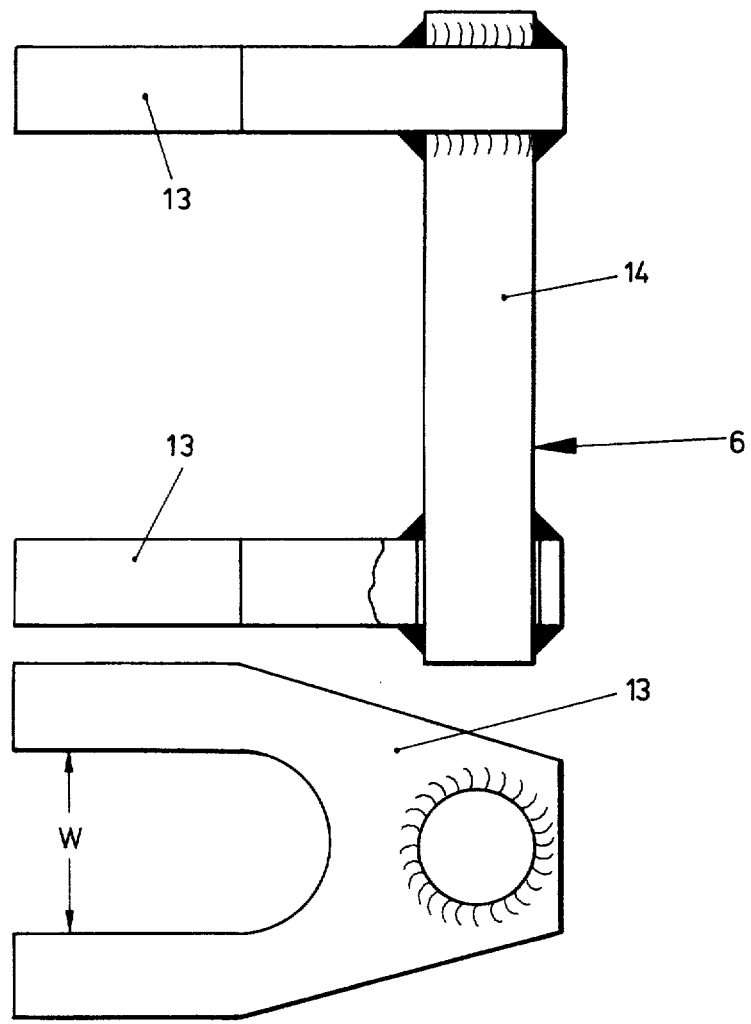
FIG. 5 shows front and lateral views of a twin load lever partially shown in FIG. 1.

The twin load lever 6 shown in detail in FIG. 5 has two aligned, fork-shaped lever arms 13 rigidly connected to one another by a bolt 14. The width W of the fork openings is dimensioned for easy insertion over the webs 9 of torsion means 3a and 3b.

Figure 4:
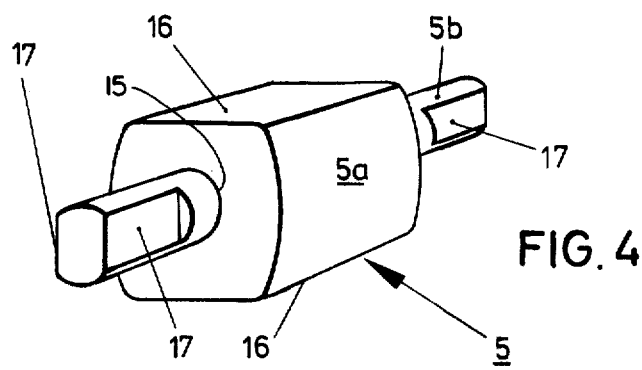
FIG. 4 shows a perspective view of a test specimen.

FIG. 4 shows the test specimen 5 in detail. It consists of a bolt 5b which is bonded to the interior of a sleeve 5a with an anaerobic adhesive. In the above torsion shear apparatus of the present invention, the adhesive strength of the adhesive is tested by subjecting the adhesive layer 15 to a torsional load. Sleeve 5a has two parallel flattened surfaces 16. The two ends of bolt 5b projecting from sleeve 5a are likewise formed with parallel flattened surfaces 17. Flattened surfaces 16 and 17 extend substantially at right angles relative to one another.

Operation and function of the torsion shear apparatus is as follows: Both ends of test specimen bolt 5b are engaged with the respective rectangular recesses 11 of torsion means 3a and 3b. The torsion means together with the test specimen are then inserted from above into bearing cradles 2a-2d, with the flattened surfaces 16 of sleeve 5a sliding along guide elements 12a, 12b of retainer 4. The rectangular recess 11 is disposed such that the flattened surfaces 10 of webs 9 extend substantially horizontally. The forked lever arms of twin load lever 6 are inserted over webs 9. A pressure plunger 18 of a universal testing machine is then lowered onto the connecting bolt 14 of the twin load lever and the force required to separate the adhesive bond is measured. The bending and pressure forces occuring in the test procedure are absorbed by bearing cradles 2a-2d, so that the ends of bolt 5b are subjected to a pure torsional load.

The invention is not restricted to the above described embodiment. It is also possible to provide only a single torsion means if it is intended to apply a torsional load to one end only of the bonded bolt. In this case the load lever consists of a single forked lever arm, and the plunger of the testing machine comes into direct engagement with the end of the lever arm. If the semicircular bearing cradles are replaced by closed bearing supports, the lever arm may be linked to the pressure plunger or traction plunger, respectively, of the testing machine for subjecting the test specimen to an alternating load. While the radial bearings 8 have been shown as ball bearings, it is also possible to employ needle bearings or friction bearings. Also, the sliding guide of the retainer means does not have to be open at the top and may be replaced by an elongate opening. While the invention is applicable with particular advantage to the testing of cylindrical test specimens, its employ with other test specimens for instance of conical shape is also possible.

I claim:

1. A torsion shear apparatus, for testing adhesives in which two members of a test specimen bonded one into the other are subjected to a torsional load, comprising rigid retainer means for non-rotatable and form-locked retention of the first member of the test specimen, an operating member rotatably mounted in a radial bearing system in horizontal alignment with the retainer means and adapted for form-locked and non-rotatable engagement with the second member of the test specimen, and torsion-applying means for rotating said operating member relative to said retainer means, characterized in that said operating member comprises a web connecting two radial bearings each supported in a bearing support, said web being engaged by a horizontal load lever forming said torsion-applying means, and in that said retainer means comprises a sliding guide portion having guide surfaces extending transversely of the radial bearings and permitting radial displacement of said first test specimen member.

2. A torsion shear apparatus according to claim 1, characterized in that the test specimen consists of a cylindrical sleeve with a bolt bonded to the interior thereof, said sleeve having two parallel flattened surface portions, and said bolt having two parallel flattened surface portions each at its ends.

3. A torsion shear apparatus according to claim 1 or 2, characterized in that the sliding guide member is disposed vertically and open at the top.

4. A torsion shear apparatus according to claim 1, characterized in that a further operating member of similar configuration is located symmetrically to said operating member on the opposite side of said retainer means, said further operating member having a second horizontal lever, the ends of said two levers being interconnected to form a twin load lever.

5. A torsion shear apparatus according to claim 1, characterized in that said web has two parallel flattened surfaces for engagement by a fork-shaped configuration of said load lever.

6. A torsion shear apparatus according to claim 1, characterized in that said web has a rectangular recess the longitudinal center axis of which coincides with the axis of rotation of said operating member.

7. A torsion shear apparatus according to claim 1, characterized in that said bearing supports are open at the top.

8. A torsion shear apparatus according to claim 1, characterized in that said bearing supports are of a closed configuration and in that said load lever is formed with a linkage connection means.

* * * * *